US00PP10338P

United States Patent [19]

Sorenson

[11] Patent Number: Plant 10,338

[45] Date of Patent: Apr. 21, 1998

[54] OSTEOSPERMUM PLANT NAMED 'CAPE DAISY VOLTA'

[75] Inventor: Carl Aksel Kragh Sorenson, Aabyhöj, Denmark

[73] Assignee: Paul Ecke Ranch, Encinitas, Calif.

[21] Appl. No.: 696,316

[22] Filed: Aug. 9, 1996

[51] Int. Cl.[6] ..... A01H 5/00

[52] U.S. Cl. ..... Plt./68.1

[58] Field of Search ..... Plt./68.1

[56] References Cited

PUBLICATIONS

UPOV–ROM Plant Variety Database 'Cape Daisy Volta', PBR OST 00013, 1994.

*Primary Examiner*—Howard J. Locker
*Assistant Examiner*—Melissa L. Kimball
*Attorney, Agent, or Firm*—Arnold, White & Durkee

[57] ABSTRACT

A new and distinct cultivar of Osteospermum named 'Cape Daisy Volta', particularly characterized by its upright growth habit with excellent light purple flower color, early flowering, medium green foliage, and suitability to 6 inch pots and 8 and 10 inch hanging basket cultures.

1 Drawing Sheet

BACKGROUND OF THE PLANT

The present invention relates to a new and distinct cultivar of plant known as Osteospermum. The new cultivar is known by the cultivar name 'Cape Daisy Volta', and was developed by the inventor Carl Aksel Kragh Sorensen in Aarhus, Denmark in 1991 by crossing 'Cape Daisy 939302' and 'Cape Daisy Ivory' unpatented plants.

Asexual reproduction by terminal (stem tip) cuttings taken by me or under my supervision at Petermiinde Greenhouse in Aarhus, Denmark, has shown that the unique features of this new Osteospermum are stabilized and are reproduced true to type in successive propagations.

The following characteristics distinguish the new Osteospermum from both its parent varieties and other cultivars of this general type known and used in the floriculture industry:

1. A unique light purple flower color.
2. An upright compact growth habit.
3. Mid season flower response.
4. Well suited for 6" pots, nursery containers, and hanging baskets.

'Cape Daisy Volta' is similar to the cultivar 'Sunny Girl' the plant described and illustrated in co-pending U.S. Plant patent application Ser. No. 08/698,337. The growth habit of 'Cape Daisy Volta' is more upright.

DESCRIPTION OF PHOTOGRAPH

The accompanying colored photograph is a top perspective view of the new cultivar, showing color as true as it is reasonably possible to obtain in a colored reproduction of this type.

DESCRIPTION OF THE PLANT

The following is a detailed description of my new Osteospermum cultivar based on plants grown under commercial practice in Encinitas, Calif. Three rooted cuttings were transplanted into 21 cm florist pots on Jan. 8, 1996. Plants were pinched on Jan. 29, 1996, and received plant growth regulator on Feb. 12 and 26. The values, measurements and observations noted below were taken from plants in bloom on Apr. 24, 1996 and continued to flower through April 1996.

On Apr. 24, 1996, I observed a plant in a 21 cm florist pot 45 cm tall. This basket had three branched plants with an overall height of 59 cm and an overall width of 65 cm. Each plant had 4 strong branches, originating from within 1.5 cm of the soil line, for a total of 12 branches. Each branch was approximately 40 cm long terminating in a flower. At observation, there were 25 flowers open and 94 flower buds in various stages of development. Four to five secondary shoots subtend the terminal flower from the top 3 nodes on the primary shoot. These secondary shoots were 23 cm in length and terminated in a flower.

Color references are made to The Royal Horticultural Society Colour Chart (R.H.S.), except where general terms of ordinary dictionary significance are used.

THE PLANT

Origin: Seedling from cross pollination.

Parentage: Cross between seed parent 'Cape Daisy 939302' and pollen parent 'Cape Daisy Ivory'.

Classification:

*Botanical.*—*Osteospermum ecklonis.*
*Common name.*—Osteospernum.
*Cultivar name.*—'Cape Daisy Volta'.

Asexual reproduction:

A. *Cutting type.*—Vegetative shoot tip with stems approximately 3 cm long and developing to 4–5 cm after 28 days in propagation.

B. *Time to initiate roots.*—8–10 days at 20° C.; nicely developed root mass in 21–28 days.

C. *Rooting habit.*—Numerous, fibrous adventitious roots from the stem base.

D. *Growth retardant application.*—Standard growth retardant application for 'Cape Daisy Volta' includes 1–2 applications of Daminozide/Butanedioic acid mono (2.2 dimethylhydrazide) at a rate of 2,500 ppm. Application are made as foliar sprays. Growth retarding chemicals generally reduce plant height by ⅓.

Plant Description:

A. *Form.*—Symmetrical, upright growing perennial shrub, with good branching characteristics after pinching, giving the plant a full appearance.

B. *Habit of growth.*—Vigorous, mounding habit, producing approximately 23 leaves per stem and terminating in flowers. Growth is determinate and flowering on secondary shoots is continuous in cool climates.

C. *Foliage description.*—1. Leaf shape: Obovate with acute tip and attenuate leaf base. 2. Leaf blade size: Mature leaves 10–12 cm long and 4–5.5 cm wide. 3. Petiole length: Approximately 3.5 cm in length. 4. Leaf Margin: Slightly sinuate 3–5 pointed lobes on either side of the leaf blade. 5. Leaf texture: Slightly undulant and twisted at the tip. i) Upper surface: Slightly pubescent with short, white trichomes evenly distributed throughout the leaf surface. ii) Under surface: Glabrous. 6. Leaf color: Green. (i) Upper surface: Darker than R.H.S. 147B. (ii) Under surface: Near R.H.S. 147B. 7. Venation: Palmately branches with a prominent light green mid-rib on the upper surface. One prominent mid-vein is slightly raised on the lower surface with two less prominent veins slightly raised on the lower surface. 8. Foliage fragrance: Characteristic Osteospermum plant fragrance, particularly notable when foliage is wet.

Flower description:

Daisy type composite flower with disk and ray florets that close at night and open in the morning. The ligulate petal of the ray floret subtends the pistil. The disk florets contain male flower parts. Florets on the flower heads are imperfect with pistillate ray florets and staminate disk florets.

*Flowering habits.*—Flowering is determinate with one primary flower at the end of a long, 18–20 cm pedicel on open flowers. Each pedicel had approximately 5 leaflets on the proximate end of the pedicel. A secondary flower arises from the base of the primary pedicel. Flowering is continuous with shoots terminating in a flower. Additional subordinate axillary shoots arise and elongae to promote additional flowerings.

*B. Natural flowering season.*—Flowering occurs primarily February through October in the northern hemisphere. Initiation occurs after a cool temperature vernalization (10–17° C.). Floriferousness may wane during hot summer days in temperature climates. Plants are initially potted using rooted cuttings, pinched two weeks later, then maintained at temperatures of 10°–12° C. for four weeks and thereafter grown for seven weeks at a temperature of 18° C., for a total of 13 weeks to flower.

*Flower buds.*—develop successively on secondary branches, reaching a size of 2 cm long and 1.5 cm wide prior to opening.

D. *Flowers borne.*—Singularly 12 cm above the plant canopy.

E. *Quantity of flowers.*—Secondary flowers occur progressively around the primary flower so that tight buds to mature flowers are visible at the same time.

F *Flower head.*—1. Number of florets: 20–26 ray florets and numerous disk florets, making up a flower disk approximately 1.5 cm in diameter. 2. Shape: Narrow linear florets with obtuse to acute tips and acute bases. Ray florets approximately 4 cm long and 1 cm wide. 3. Color: Ray florets are light purple; disk florets are violet-blue. (i) Upper surface of ray florets: Near R.H.S. 75C at the tip and fading to R.H.S. 75D near the base of the florets. (ii) Under surface of ray florets: Longitudinal stripes near R.H.S. 174C alternating with stripes near R.H.S. 83C. (iii) Disk florets: Near R.H.S. 89B. 4. Surface: (i) Upper surface of ray florets: Glabrous. (ii) Under surface of ray florets: Glabrous but pubescent near the base. 5. Flower Head Size: Up to 8.2 cm in diameter. 6. Flower Fragrance: None.

G. *Reproductive organs.*—1. Stamens: Short stamens emerge on outer most disk florets and progress toward the center. 1. Stamens: Short stamens emerge on outermost disk florets and progress toward the center. 2. Anther: Each disk floret has 1 stamen terminating in a 5-part anther. 3. Pollen: Copious and golden yellow. 4. Stigma: Bipartite. 5. Styles: Short, approximately 2–3 mm long and purple. 6. Ovary: Inferior to petals and green in color.

H. *Resistance.*—1. Frost: Withstands light frost. 2. Root, stem, foliage and flower diseases: High resistance.

What is claimed is:

1. A new and distinct cultivar of Osteospermum plant named 'Cape Daisy Volta', as illustrated and described.

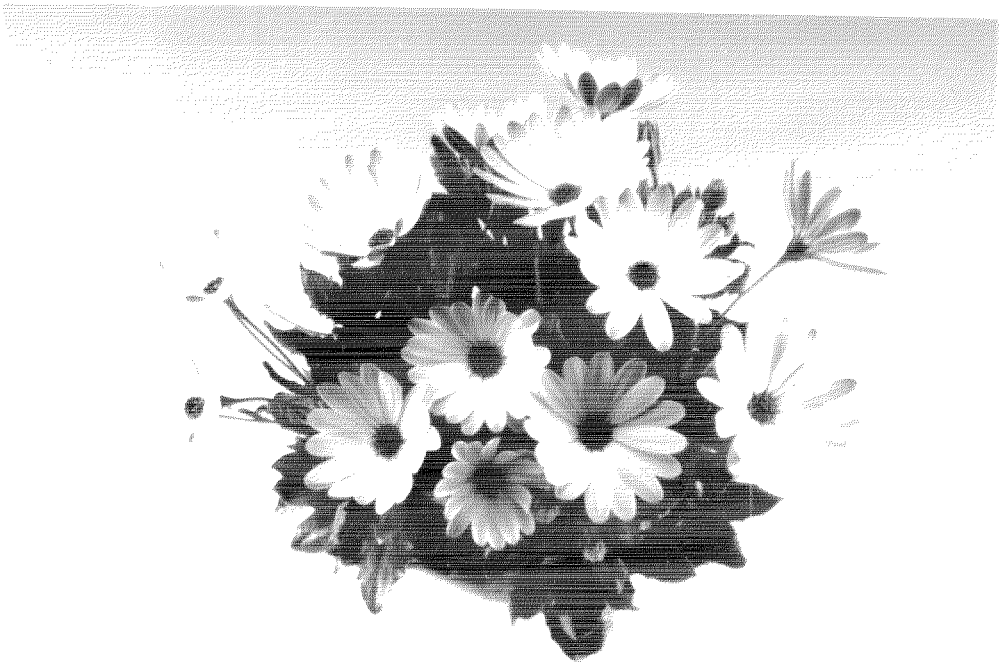

* * * * *